US005580433A

United States Patent [19]
Baker et al.

[11] Patent Number: 5,580,433
[45] Date of Patent: Dec. 3, 1996

[54] SELECTIVE ELECTROCHEMICAL DETECTOR FOR NITRIC OXIDE AND METHOD

[76] Inventors: Charles K. Baker, 902 Riverstone, San Antonio, Tex. 78258; Mohan R. A. Ram, 1455 Cable Ranch Rd., #2113, San Antonio, Tex. 78254; Stephen T. Wellinghoff, 7718 Benbrook, San Antonio, Tex. 78250

[21] Appl. No.: 540,849

[22] Filed: Oct. 11, 1995

Related U.S. Application Data

[62] Division of Ser. No. 232,378, Apr. 25, 1994, Pat. No. 5,466,350, which is a division of Ser. No. 126,233, Sep. 24, 1993, Pat. No. 5,409,591.

[51] Int. Cl.$^6$ .................................................... G01N 27/26
[52] U.S. Cl. ..................... 204/425; 204/412; 204/415; 204/426; 204/192.15; 204/192.22
[58] Field of Search ..................... 204/192.15, 192.22, 204/424, 425, 415, 412, 426, 153.14

[56] References Cited

U.S. PATENT DOCUMENTS

| | | | |
|---|---|---|---|
| 4,182,667 | 1/1980 | Dobson et al. | 204/418 |
| 5,124,021 | 6/1992 | Kaneyasu et al. | 204/425 |
| 5,141,614 | 8/1992 | Akridge et al. | 204/192.15 |
| 5,202,201 | 4/1993 | Meunier et al. | 204/192.29 |

FOREIGN PATENT DOCUMENTS

0257842A2  2/1988  European Pat. Off. .

OTHER PUBLICATIONS

Logothetis et al., "High–Temperature Oxygen Sensors Based on Electrochemical Oxygen Pumping", *Fundamentals and Applications of Chemical Sensors*, Chapter 8 (1986), American Chemical Society. No Month Available.
Liu et al., "Limiting–Current Chlorine Gas Sensor Based on Beta–Alumina Solid Electrolyte", *Sensors and Actuators*, (B.6) (1992), pp. 270–273. No Month Available.
Nobugai et al., "Preparation of Beta–Alumina Thin Film by RF–Sputtering", *Materials Science Monographs*, Part B: React. Solids, VC28B (1985), pp. 811–816. No Month Available.
Matsuura et al. "Mechanism of Gas Sensitivity Change with Time of $SnO_2$ Gas Sensors", *Sensors and Actuators*, 14 (1988), pp. 223–232. No Month Available.
Ishihara et al., "Selective Detection of Nitrogen Monoxide by the Mixed Oxide of $Cr_2O_3$–$NHb_5O_5$", *Chemistry Letters*, (The Chemical Society of Japan), 1988, pp. 997–1000. No Month Available.
Egashira et al., "Oxygen Desorption and Conductivity Change of Palladium–Doped Tin (IV) Oxide Gas Sensor", *Fundamentals and Applications of Chemical Sensors*, Chapter 4, 1986, American Chemical Society. No Month Available.

(List continued on next page.)

*Primary Examiner*—Bruce F. Bell
*Attorney, Agent, or Firm*—Crutsinger & Booth

[57] ABSTRACT

A thin film solid state amperometric detector for nitric oxide is provided based upon a mobile cation electrolyte that selectively transmits nitrosonium cations (NO*) therethrough. The presently most preferred embodiment employs NO-β-alumina as the mobile cation electrolyte. The electrodes of the detector are preferably arranged in a bipotentiostat arrangement. The first and second working electrodes share a common reference electrode and a common counter electrode, which are positioned such that the potentials of the first and second working electrodes can be independently controlled. The first working electrode is exposed to a fluid (liquid or gaseous), whereas the second working electrode is normally isolated from the fluid. The first working electrode is set at a potential capable of oxidizing NO to NO+, the NO+ moves through the mobile cation solid electrolyte to the second electrode, and the second working electrode is set at a potential capable of reducing the NO+ back to NO. The detector has a diffusion barrier for the nitric oxide so that the voltage-current characteristics of the detector under diffusion limiting conditions are proportional to the concentration of nitric oxide in a fluid.

10 Claims, 5 Drawing Sheets

OTHER PUBLICATIONS

Takeuchi, "Oxygen Sensors", *Sensors and Actuators*, 14 (1988), pp. 109–124. No Month Available.

Lantto, et al., "A study of the Temperature Dependene of the Barrier Energy in Porous Tin Dioxide", *Sensors and Actuators*, 14 (1988), pp. 149–163. No Month Available.

Sberveglieri et al., "Radio Frequency Magnetron Sputtering Growth and Characterization of Indium–Tin Oxide (ITO) Thin Films For $No_2$ Gas Sensors", *Sensors and Actuators*, 15 (1988), pp. 235–242. No Month Available.

Tierney et al., "Fast–Response Gas Sensors", *Sensors*, Oct. 1992, pp. 12–19.

Bontempelli et al., "Electrode Processes of Oxygenated Nitrogen Compounds in Acetonitrile Medium, Part I. Nitrogen Oxides", *Electroanalytical Chemistry and Interfacial Electrochemistry*, 55 (1974), pp. 91–100. No Month Available.

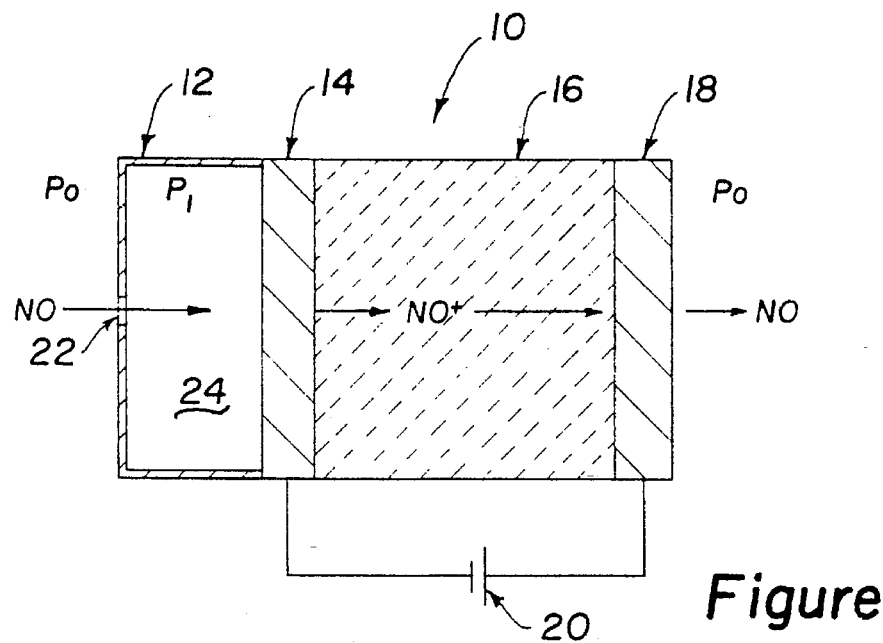
Figure 1
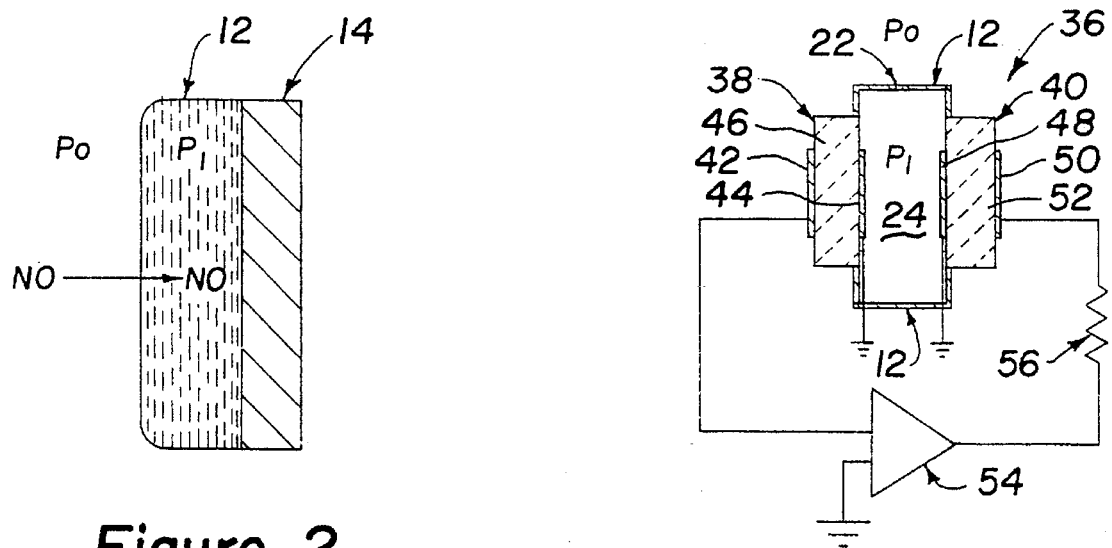
Figure 2
Figure 4
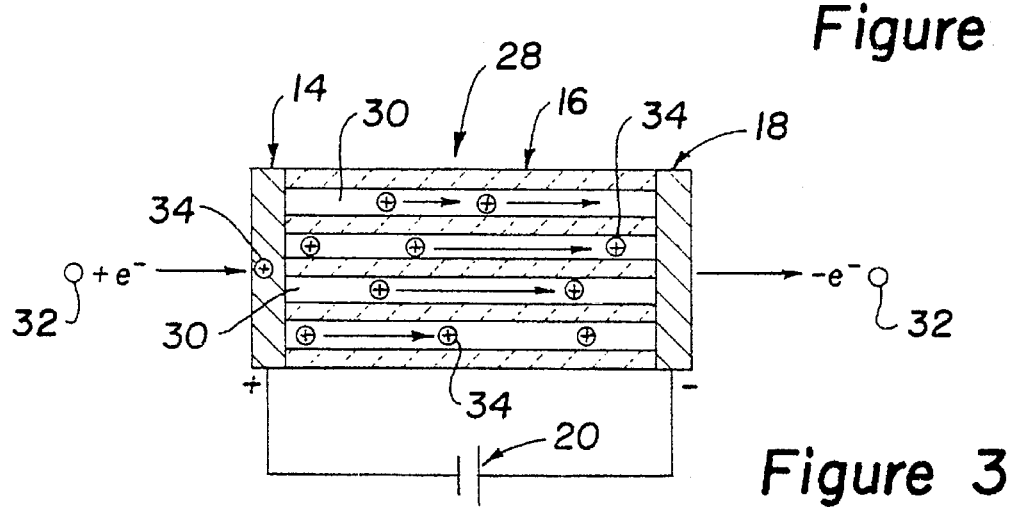
Figure 3

Step 1:

Step 2:

1

SELECTIVE ELECTROCHEMICAL DETECTOR FOR NITRIC OXIDE AND METHOD

This application is a division of application Ser. No. 08/232,378, filed Apr. 25, 1994; issued as U.S. Pat. No. 5,466,350, which is a divisional of U.S. Ser. No. 08/126,233, filed Sep. 24, 1993; issued as U.S. Pat. No. 5,409,591 on Apr. 25, 1995 entitled SELECTIVE ELECTROCHEMICAL DETECTOR FOR NITRIC OXIDE AND METHOD.

TECHNICAL FIELD

The invention relates to electrochemical detectors and methods for selectively detecting nitric oxide (NO) in a fluid mixture. More particularly, the invention relates to electrochemical detectors and methods that employ a mobile ion electrolyte for selectively detecting an ionized chemical species.

BACKGROUND OF THE INVENTION

Selective electrochemical detectors have numerous applications in diverse technical areas. For example, such detectors can be used to detect inorganic combustion products in the exhaust gas of natural gas combusters, internal combustion engines, and various types of heating furnaces and boilers. Electrochemical detectors also have applications for detecting and quantifying the concentration of various components in chemical plant or petrochemical refinery processes. Furthermore, such detectors have medical applications, for example, detecting anesthetic gas (laughing gas) or measuring oxygen levels in blood. The detectors can be used for automated process control and for continuous monitoring of environmental pollutants. In particular, the determination of nitric oxide is very important for many different reasons. Nitric oxide is toxic at high concentrations, and its release into the atmosphere causes many environmental concerns. It can also be valuable to monitor nitric oxide in the exhaust stream produced by the combustion of organic fuels.

One of the most common types of detectors for nitric oxide in the exhaust gas of natural gas combusters, internal combustion engines, and various types of heating furnaces employs chemiluminescence of excited states generated by the reaction of nitric oxide with oxygen, hydrocarbons, or carbon oxides on a catalytic surface. However, these chemiluminescence detectors have long term stability problems and a rather complicated electronics system. Thus, there is a need for a more stable and less complicated detection system for nitric oxide in the exhaust gas from a combustion process.

Another type of nitric oxide detector is of semiconductive type. Semiconductive gas sensors employ a polycrystalline-oxide semiconductor material that is coated with porous metal electrodes to form a semiconductor "sandwich." The semiconductor material is typically formed, for example, of $SnO_2$ or $ZnO$. The porous electrodes are typically formed of platinum and are used for measuring the conductivity of the semiconductor material. When gases, such as oxygen ($O_2$), nitric oxide (NO), nitrogen dioxide ($NO_2$), carbon monoxide (CO), and methane ($CH_4$, natural gas) are absorbed on the surface of a semiconductor material the electrons in the conduction band of the polycrystalline oxide are pinned in $O^{2-}$ surface states, which changes the conductivity of the semiconductor material. The surface conductivity of each semiconductor particle is slightly reduced through an interparticle barrier potential that depends upon the partial pressure of oxygen or other electron accepting gas absorbed on the semiconductor material. V. Lantto, R. Pomppainen, and S. Leppavouri, *Sensors and Actuators*, 14, 149 (1988). It appears that the sensitivity of the detector depends upon the enthalpy of the gas absorption onto the surface of the semiconductor, which determines coverage as a function of gas partial pressure and the ease of electron transfer to the gas molecule.

Although semiconductive gas sensors often have good sensitivity and fast response time, this type of detector is normally limited to operation at temperatures below about 300° C. and usually does not show long-term stability. The limitation to relatively low operating temperatures makes this type of detector susceptible to extraneous effects that include "memory effects" and temperature dependent water absorption. The memory effects are a function of the reversibility of the absorption of the gas particle on the surface of the semiconductor material, which typically requires that the semiconductive gas sensor to be operated at above 200° C. to achieve complete reversibility of absorption.

Furthermore, the gas sensors of the semiconductive type are rarely selective to particular chemical species. However, at least one semiconductor material, $In_2O_3$–$SnO_2$ (9:1 ratio by weight), has been reported to be selective to nitrogen dioxide ($NO_2$) at temperatures of 200°–350° C. G. Sberveg-tierei, S. Groppelli, and G. Coccoli, *Sensors and Actuators*, 15, 235 (1988). Recently, a $Cr_2O_3$–$Nb_5O_5$ semiconductive type detector with high selectivity for nitric oxide (NO) in the presence of nitrogen dioxide, carbon monoxide, and carbon dioxide has been reported. T. Ishihara, K. Shiokawa, K. Eguchi, and H. Arai, *Chem, Lett.*, 997 (1988). However, the selectivity of this detector maximizes at 200° C. and disappears completely at 500° C. The loss of selectivity at high temperatures is induced by desorption and reduction of the semiconductor surface. In general, the strong temperature dependence of the selectivity and the small conductivity changes induced by the surface adsorption process have limited the use of this type of detector for quantitative measurements of nitric oxide.

A modified electrochemical oxygen detector has also been reported for the detection of nitric oxide in a gaseous mixture. One of the most accurate oxygen sensors known in the art is of the limiting current type, which employ the principle of an electrochemical pumping cell; E. M. Logothetis and R. E. Fietrick, in "Fundamentals and Applications of Chemical Sensors", Chapter 4, ACS Symposium Series, 309, 71 (1986).

In a typical oxygen sensor of the limiting current type yttrium ($Y_2O_3$) stabilized zirconium ($ZrO_2$) is used in an oxygen pumping cell as a solid electrolyte that allows for mobile oxygen anions. Oxygen enters the pumping cell through a porous "front" electrode that is polarized so that oxygen is reduced to $O^{2-}$, moves through the electrolyte in this form, and then is oxidized back to $O_2$ at the porous "back" electrode. The rate at which oxygen is pumped from the front electrode to the back electrode increases with increasing applied voltage across the electrodes.

A diffusion barrier is positioned between the analyte gas and the porous front electrode of the oxygen pumping cell. Diffusion barriers can be of the aperture type, the porous media type, or combinations thereof. Porous media include ceramics, micromachined materials, and polymers.

The diffusion rate of oxygen through the diffusion barrier from the analyte gas to the 'front' electrode of the pumping cell is determined by the overall geometry of the detector, the diffusion constant of the barrier, and the partial pressure of oxygen in the gas. The diffusion constant for a particular diffusion barrier and a particular chemical species is further dependent on a plurality of factors, including temperature, However, at a constant temperature of operation, the diffusion rate is essentially proportional to the partial pressure of oxygen in the analyte gas.

The ionic oxide current in the oxygen pumping cell increases with applied voltage until complete oxygen depletion occurs at the "front" electrode. To obtain a limiting current, the oxygen pumping cell of the electrochemical detector must be able to pump oxygen from the front electrode through the electrolyte to the back electrode at a faster rate than oxygen can diffuse through the diffusion barrier to the front electrode. Thus, the limiting current type of detectors typically operate in temperature ranges above 400° C. where the ionic conductivity through the electrolyte is high. The value of the limiting current will depend upon the rate of diffusion of oxygen through the diffusion barrier to the front electrode, which under constant temperature operating conditions is proportional to the partial pressure of oxygen in the analyte gas. Thus, the limiting current is proportional to the partial pressure of oxygen in the analyte gas.

A more advanced form of the ionic current sensor involves two electrochemical cells, one for sensing and one for ion pumping. In this configuration, the ion pump is used to deplete a substantially closed space of oxygen, setting up an oxygen partial pressure difference between the front and back surface of the sensing electrode that acts as a Nernst concentration cell. The current-voltage relationship for the double cell depends on the external oxygen partial pressure and on diffusion and geometric characteristics as before but with advantages over the single cell configuration, which include: less temperature dependence; lower current and voltage operation (less electrode polarization and decomposition); and operation in any region of the current-voltage curve.

The recent modification of the double cell oxygen detector for determining the concentration of $NO_x$ employs a unibody construction made from yttria stabilized zirconia that consists of four cells. M. Node, N. Karo, and H. Karachi, European Patent Application No. EP 87306846.4, Publication No. 257,842, Mar. 3, 1988. One such double cell consists of a conventional oxygen pumping and oxygen sensing arrangement as discussed above, while the other double cell also consists of pumping electrodes and sensing electrodes, but with one of the platinum electrodes coated with rhodium. The rhodium will catalytically decompose nitric oxide (NO) and nitrogen dioxide ($NO_2$) into nitrogen ($N_2$) and oxygen ($O_2$) at the operating temperature of 500° C. and increases the partial pressure of oxygen detected at the sensing electrodes versus that detected at the oxygen sensor. The reference electrode part of both sensing elements is exposed to a constant reference pressure of oxygen. In this four cell arrangement the oxygen produced by selective decomposition of the oxides of nitrogen is read directly as a sensing voltage difference between Nernst cells. Thus, $NO_x$ can be selectively detected with the oxygen content of the gas stream internally compensated. However, the sensor cannot distinguish between nitric oxide (NO) and nitrogen dioxide ($NO_2$). Moreover, the platinum electrodes of a common oxygen sensor are capable of a catalytic function with respect to other reductive gas components, such as carbon monoxide (CO). In the case where the measurement gas contains one or more reductive components (including CO, for example), the operation of this detector requires that the concentration of the reductive components, which affect the oxygen partial pressure, be known. Thus, the detector cannot be considered to have much selectivity. These are severe limitations on the usefulness of this type of detector.

Thus, there is a long-felt need for a stable detector that is highly selective to nitric oxide and capable of operating over a wide temperature range. For gas sensing applications, there is further a long-felt need for a stable detector capable of operating at elevated temperatures, particularly at temperatures above 300° C. There is also a need for a low cost, relatively uncomplicated nitric oxide detection system.

SUMMARY OF THE INVENTION

According to one aspect of the present invention, an electrochemical nitric oxide detector is provided that includes at least the following: a first electrode that can be given a potential sufficiently large to oxidize nitric oxide (NO) to nitrosonium cation ($NO^+$; a second electrode that can be given a potential sufficient for reducing nitrosonium cations ($NO^+$) to nitric oxide (NO), the second electrode being spaced apart from the first electrode; and a solid electrolyte having mobile niitrosonium cation ($NO^+$) cations, the electrolyte being positioned between the first and second electrodes.

The mobile cation solid electrolyte comprises a matrix of artionic and cationic chemical species. The molecular structure of the electrolyte includes layers, channels, or passages that are sparsely populated with cations that can move through the solid material under an electric field gradient. The geometry of the molecular structure is such that the size and steric effects determine which cationic species can move through the material. Thus, the molecular structure makes the solid electrolyte highly selective to the relatively small nitrosonium cations such that virtually any other species that might be oxidized at the first electrode would be too large or have too much steric hindrance to move through the channels. In particular, because the oxidation and reduction potentials of NO to $NO^+$ and $NO_2$ to $NO_2^+$ are so similar, the discrimination against the movement of the larger nitryl cations ($NO_2^+$) through the electrolyte is employed to selectively determine NO in the presence of $NO_2$ (and its dimer, $N_2O_4$.

The most developed mobile cation electrolyte materials include alkali metal doped β-aluminas ($Al_2O_3$) that consist of close packed spinel layers with bridging layers sparsely populated by alkali metal cations and oxide anions. For example, the sodium ions in the Na-β-alumina structure can be ion exchanged with silver, potassium, rubidium, ammonium, or nitrosonium cation ($NO^+$) ions. Other mobile cation electrolyte materials include β-ferrites ($Fe_2O_3$) and α-corundum ($Cr_2O_3$). It is also anticipated that organic based mobile cation electrolyte materials, such as Nation (TM) (a perfluorosulfonate polymer) or polyethylene oxide, would have a suitable molecular structure for conducting nitrosonium cations to the exclusion of other cations that are too large or have too much steric hindrance to move through the channels of electrolyte structure. Typically the ionic conductivity, i.e., the mobility of ions through the solid electrolyte, increases with increasing temperature.

In operation, the electrochemical detector is exposed to a fluid that my include nitric oxide. The fluid can be gaseous or liquid, although for most applications it is typically gaseous. If nitric oxide comes into contact with the first electrode, it is first oxidized to nitrosonium cation, and the cation is moved by the electric field between the first and second electrodes through the solid electrolyte to the second electrode, where it is reduced back to nitric oxide. The current-voltage characteristics of the electrochemical detector can be used to detect the presence of nitric oxide in the fluid.

The configuration of the electrochemical detector can be any one of several conventional designs. For example, it can be similar to a conventional electrochemical oxygen detector of the limiting current type, employing a nitric oxide pumping cell arrangement instead of an oxygen pumping cell. A diffusion barrier is positioned between the first electrode and the fluid such that the overall geometry of the detector and the diffusion constant of the barrier for nitric oxide such that the diffusion rate for nitric oxide through the barrier is diffusion limited and proportional to the concentration of nitric oxide in the fluid. The diffusion constant is temperature dependent, so the detector should be maintained at a stable temperature. The ionic oxide current increases with applied voltage until complete nitric oxide depletion occurs at the first electrode. The value of the limiting current will depend upon the geometric characteristics of the detector and diffusion constant of the nitric oxide through the diffusion barrier above the tint electrode and the partial pressure or concentration of nitric oxide in the fluid.

The detector can be similar to the double cell electrochemical detector for oxygen, one cell for sensing and the other for pumping. In this configuration, the ion pumping cell is used to deplete a substantially closed space of nitric oxide, setting up a nitric oxide partial pressure difference between the front and back surfaces of the first electrode of the sensing cell that acts as a Nernst concentration cell. The current-voltage relationship for the double cell depends on the external nitric oxide pressure and on diffusion and geometric characteristics as before but with advantages over the single cell configuration, which include: less temperature dependence; lower current and voltage operation (less electrode polarization and decomposition); and operation in any region of the current-voltage curve.

In another aspect of the invention, the electrochemical detector is configured in a bipotentiostat arrangement. The first electrode would be considered to be the first working electrode of the bipotentiostat, and the second electrode would be considered to be the second working electrode of the bipotentiostat. The first and second working electrodes share a common reference electrode and a common counter electrode, which are positioned such that the potentials of the first and second working electrodes can be independently controlled. The first working electrode is exposed to the analyte fluid, whereas the second working electrode is normally isolated from the analyte fluid. The first working electrode is set at a potential capable of oxidizing NO to $NO^+$, the $NO^+$ moves through the mobile cation solid electrolyte to the second electrode, and the second working electrode is set at a potential capable of reducing the $NO^+$ back to NO. Thus, under diffusion limited conditions, the current through the second working electrode will be proportional to the concentration of NO in the fluid.

The bipotentiostat configuration of the electrochemical detector provides additional control, selectivity, and current-voltage information, which are important to more accurately and selectively quantify the concentration of nitric oxide in the fluid exposed to the first working electrode.

These and other features, advantages, and objects of the present invention will be apparent to those skilled in the art upon reading the following detailed description of preferred embodiments together with the drawings.

BRIEF DESCRIPTION OF THE DRAWING

The accompanying drawings are incorporated into and form a part of the specification to illustrate several examples of the present invention. These drawings together with the description serve to explain the principles of the invention. The drawings are only for the purpose of illustrating preferred and alternative examples of how the invention can be made and used and are not to be construed as limiting the invention to only the illustrated and described examples. The various advantages and features of the present invention will be apparent from a consideration of the drawings in which:

FIG. 1 is a cross-section diagram of a limiting current type electrochemical detector having a diffusion barrier and a pumping cell;

FIG. 2 illustrates the cross-section of a diffusion barrier of the porous media type for the limiting current type electrochemical detector shown in FIG. 1;

FIG. 3 is a conceptual representation of the molecular structure of a mobile cation solid electrolyte;

FIG. 4 is a simplified schematic of a double-cell electrochemical detector;

DETAILED DESCRIPTION OF PREFERRED EMBODIMENTS

Figure 6:
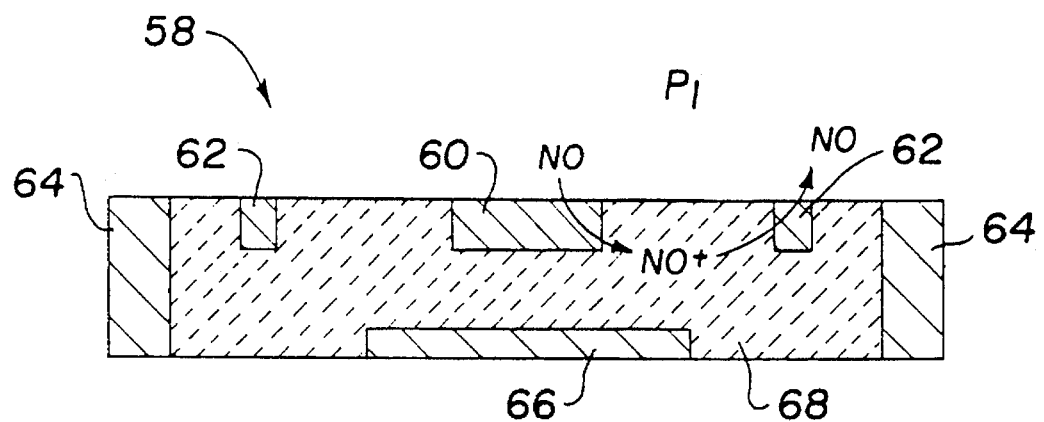
FIG. 6 is a top plan view of the bipotentiostat configuration shown in FIG. 5.

The present invention will be described by referring to apparatus and methods showing various examples of how the invention can be made and used. Like reference characters are used throughout the several views of the drawing to indicate like or corresponding parts.

As used herein, the term 'fluid' is used in its ordinary sense to include any material in either a liquid or gaseous state. The present invention is anticipated to have widest application for the detection of nitric oxide in gaseous mixtures, therefore, the concentration of nitric oxide in a fluid is frequently referred to in terms of partial pressure. It is to be understood, however, that the concentration of nitric oxide in a fluid may be expressed in any convenient units of measurement. As used herein, the term "analyte fluid" refers to any fluid for which the presence of nitric oxide is being determined.

FIG. 1 of the drawing illustrates the cross-section of an electrochemical detector of the limiting current type that employs a pumping cell for nitric oxide according to one aspect of the invention, generally referred to by the reference numeral 10. The limiting current detector 10 includes a diffusion barrier 12, electrode 14, a mobile cation solid electrolyte 16, and electrode 18. Electrodes 14 and 18 are formed of any conducting, porous material, for example, porous platinum. Electrodes 14 and 18 are electrically connected across a voltage source 20. The diffusion barrier 12 of the detector 10 is exposed to the analyte fluid, which may include a partial pressure of nitric oxide, represented by $P_0$.

The analyte species, NO, is oxidized at electrode 14. Under the influence of an electric field generated by the potential difference between electrode 14 and electrode 18, the nitrosonium cation, $NO^+$, moves through the channels of the solid electrolyte 16. At electrode 18 the nitrosonium cation is reduced back to nitric oxide, and emerges from the porous electrode 18 back into the analyte fluid. The limiting current of nitrosonium cations through the electrolyte 16 is determined by the rate of diffusion through the diffusion barrier 12, and the voltage-current characteristics of the electrochemical detector 10 my be used to quantitate the partial pressure of nitric oxide, $P_0$, in the analyte fluid.

Continuing to refer to FIG. 1 of the drawing, it can be seen that the nitric oxide in the analyte fluid can diffuse through a tiny aperture, such as a pin hole 22, into a cavity 24. The electrodes 14 and 18, electrolyte 16, and voltage source 20 operate as a nitric oxide pumping cell that removes the nitric oxide from the cavity 24, thereby reducing the partial pressure of nitric oxide within the cavity to $P_1$. The nitric oxide pumping cell is capable of pumping nitric oxide from the cavity 24 at a faster rate than it can diffuse into the cavity through the pin hole aperture 22 of the diffusion barrier 12, thus the diffusion rate of nitric oxide is the limiting factor in determining the current through the pumping cell. As previously described, the diffusion rate of nitric oxide through the diffusion barrier is proportional to the partial pressure $P_0$ of the nitric oxide and temperature. Thus, so long as the detector 10 is maintained at a constant temperature, it is capable of quantifying the partial pressure of nitric oxide, $P_0$.

Referring now to FIG. 2 of the drawing, a partial view of a limiting current detector 10 is shown with an alternative example of the diffusion barrier 12. FIG. 2 shows a diffusion barrier comprising a material that is at least partially porous to nitric oxide. Suitable porous media include, for example, ceramics, micromachined materials, and polymers. This material is preferable capable of withstanding elevated temperatures and chemical attack by any species that might be in the analyte fluid.

The limiting current, $I_L$, for the detector 10 is defined by the following equation:

$$I_L = ne\sigma_L P_0 \quad (1)$$

where ne is the number of electrons, $\sigma_L$ is the barrier constant for the diffusion barrier, and $P_0$ is the partial pressure of the nitric oxide in the analyte gas.

FIG. 3 illustrates an electrochemical cell 28 having an electrode 14, an mobile cation solid electrolye 16, and an electrode 18. Electrodes 14 and 18 are connected across a voltage source 20. The structure of the solid electrolyte 16 has representationally illustrated channels 30. A chemical species in the analyte fluid, represented by a circle 32, has an outer valence electron represented by $e^-$. When the species 34 moves through the porous material of electrode 14, the outer valence electron $e^-$ on the species 32 is removed to produce a charged particle 34. Charged particles 34 moves under the electric field between the electrode 14 and the electrode 18 through the channels 30 of the solid electrolyte 16. When a charged particle 34 passes through the porous electrode 18, an outer valence electron $e^-$ is provided to reduce the cation back to a neutral molecule.

The geometry of the molecular structure of the solid electrolyte 16 is such that size and steric effects determine which cationic species can be moved through the channels 30. Thus, the molecular structure makes the electrolyte 16 highly selective to the relatively small nitrosonium cations 34 such that virtually any other species that might be oxidized at the first electrode 14 would be too large or have too much steric hindrance to move through the channels 30.

In a presently most preferred embodiment of the invention, the solid electrolyte 16 comprises alumina, which provides for the selective mobility of NO* cations through the electrolyte. If larger cations were to be ion-exchanged into the molecular structure to replace the nitrosonium cations, the steric considerations usually require a change in the molecular structure, which if it can be accomplished at all, takes place under extreme conditions, as will be hereinafter described for the ion-exchange of nitrosonium cations for sodium ions in the β-alumina structure. The molecular structure of non-amorphous materials can be characterized by well known X-ray diffraction techniques.

In another embodiment of the invention shown in FIG. 4, mobile cation solid electrolyte is employed in a dual cell electrochemical detector, generally referred to by the numeral 36. This alternative configuration for an electrochemical detector includes a first electrochemical cell 38 and a second electrochemical cell 41). The first electrochemical cell 38 includes a pair of electrodes 42 and 44 being separated by a mobile cation solid electrolyte 46. Similarly, the second electrochemical cell 40 includes a pair of electrodes 48 and 50 being separated by a mobile cation solid electrolyte 52. Electrode 42 of the first cell 38 and 50 of second cell 40 are electrically connected through feedback amplifier 54 and resistor 56.

The dual cell detector 36 includes a diffusion barrier 12, which can be of the aperture or porous media type. For example, the detector 36 illustrated in FIG. 5 employs a diffusion barrier 12 defining a cavity 24 between the two cells of the detector, the cavity having a small aperture 22 that can be exposed to the analyte fluid, which can have a partial pressure $P_0$ of nitric oxide. The rate of diffusion of nitric oxide through the aperture 22 is governed by the same factors previously discussed.

In the configuration shown in FIG. 4, the one of the first and second electrochemical cells is used as a nitric oxide pumping cell to deplete the cavity 24 of nitric oxide and the other of the two cells is used as a sensing cell, thereby setting up a nitric oxide partial pressure difference between the front and back surfaces of the first electrode of the sensing cell that acts as a Nernst concentration cell. The current-voltage relationship for the dual cell electrochemical detector 36 depends on the external nitric oxide partial pressure P, and on diffusion and geometric characteristics as before but with advantages over the single cell configuration, which include: less temperature dependence; lower current and voltage operation (less electrode polarization and decomposition); and operation in any region of the current-voltage curve.

Figure 5:
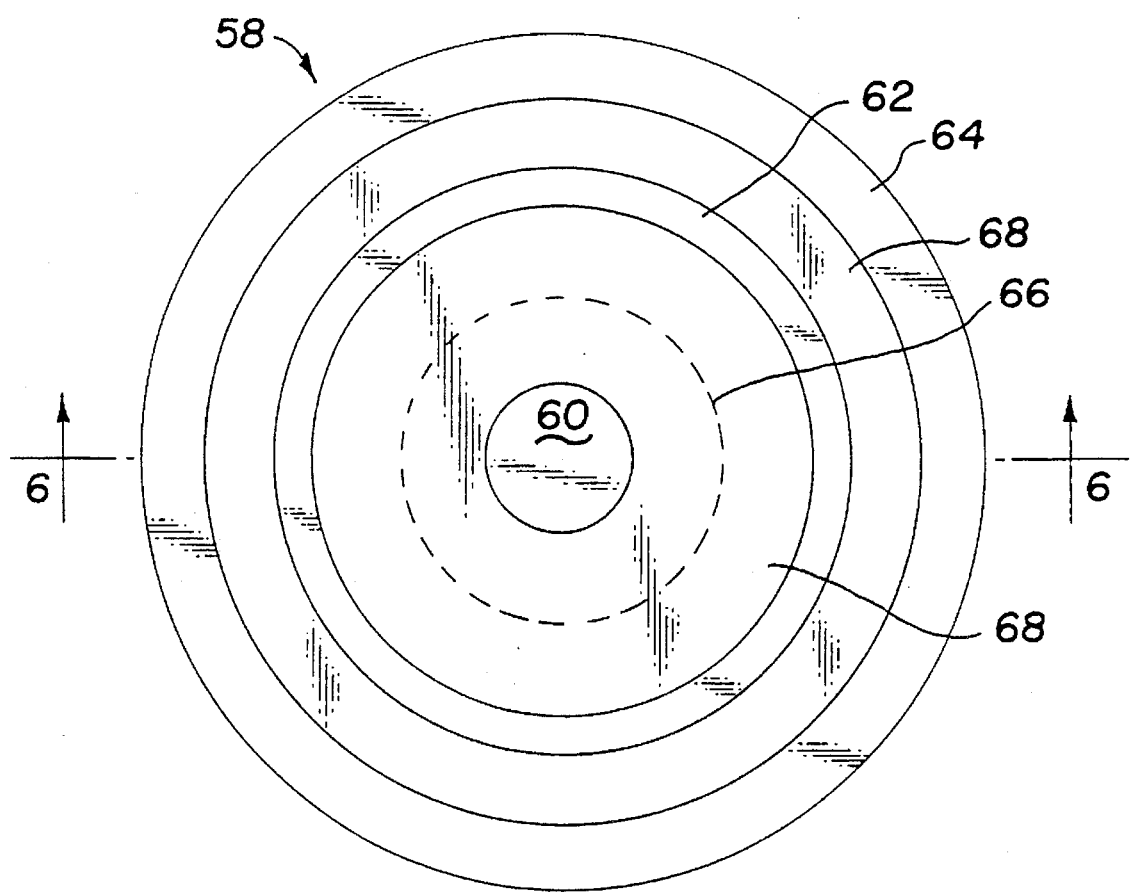
FIG. 5 is a side cross-section of a bipotentiostat arrangement for an electrochemical cell.

FIGS. 5 and 6 of the drawing illustrate another aspect of the invention in that mobile cation solid electrolyte is employed in a bipotentiostat electrochemical detector, generally referred to by the numeral 58. FIG. 5 is a cross-section view of the bipotentiostat electrochemical detector, and FIG. 6 is a top plan view of the detector 58. Two independently controlled working electrodes 60 and 62 share common reference electrode 64 and a common counter electrode 66. The electrodes are separated by mobile cation solid electrolyte 68. For the purposes of simplifiying FIGS. 5 and 6, a diffusion barrier limiting the flow of nitric oxide to the working electrode 60 is not shown.

Working electrode 60 is set at a potential able to oxidize NO to $NO^+$, and working electrode 62 is set at a potential able to reduce $NO^+$ to NO. Under diffusion limited conditions, the electric current though the reduction electrode 62 is proportional to the partial pressure $P_0$ of nitric oxide.

In the presently most preferred embodiment of the invention shown in FIGS. 5 and 6 the four electrodes 60, 62, 64, and 66 have a concentric circle geometry. However, it is to be understood that other bipotentiostat electrode geometries can be employed. The working electrodes 60 and 62, counter electrode 64, and reference electrode 66 can be independently formed of any conducting material, including without limitation carbonaceous material, silver, platinum, palladium, or gold and mixtures thereof. Furthermore, the working electrodes 60 and 62 are preferably porous so that nitric oxide and nitrosonium cations can diffuse therethrough.

Figure 7:
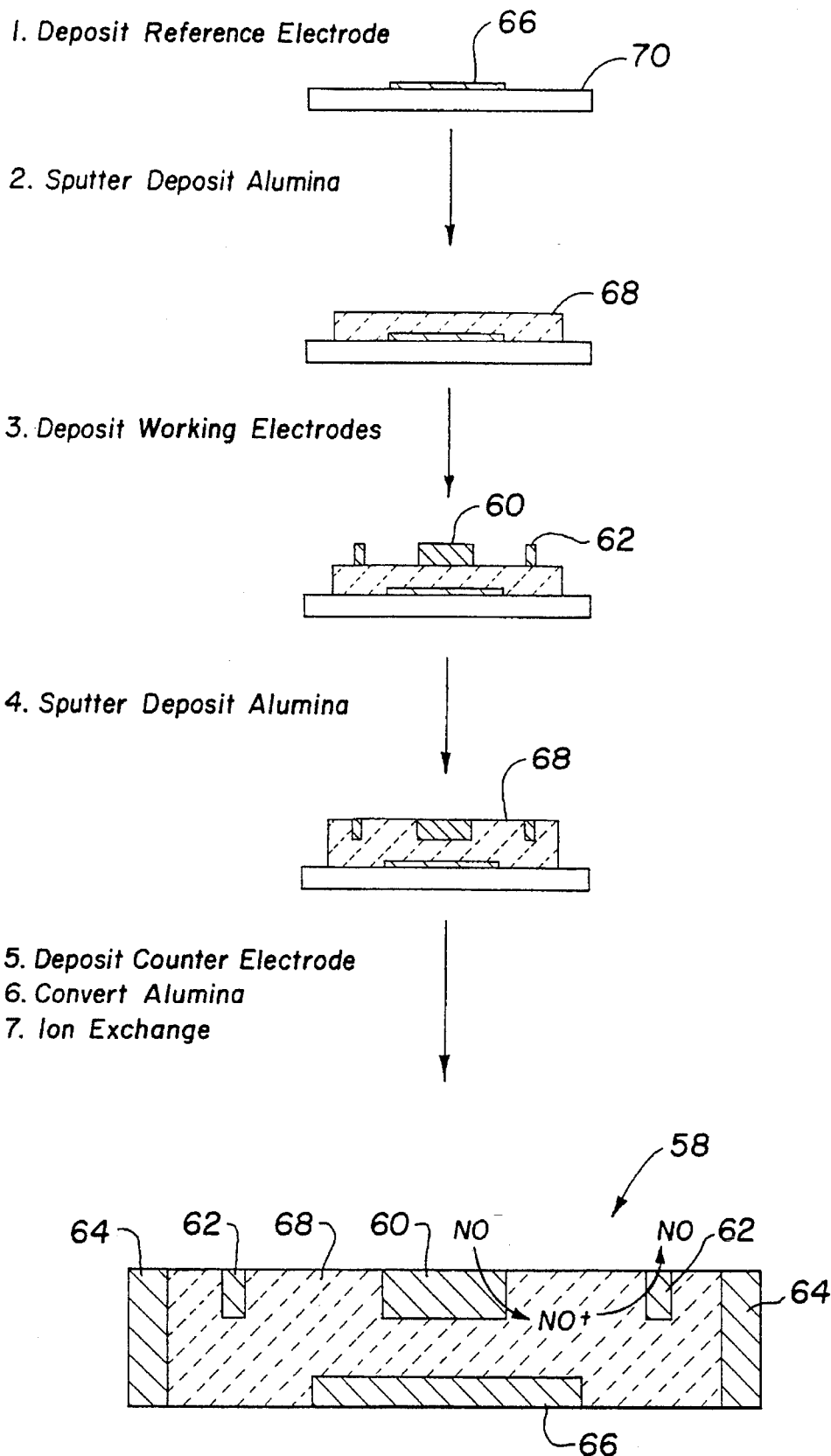
FIG. 7 shows the steps for making the bipotentiostat configuration shown in FIG. 5.

The bipotentiostat arrangement of the electrochemical detector 58 allows independent control of the potential and current applied to working electrodes 60 and 62. To operate in a sensor mode, the potential of electrode 60 can be set to a value such as to cause the desired oxidation reaction of nitric oxide. The potential of electrode 62 can be set to a value such as to cause the reduction of the oxidized nitric oxide. The concentration of nitric oxide in the analyte fluid can be determined by monitoring the current at 62 under diffusion limited conditions. The available electrochemical literature on the oxidation of NO→$NO^+$ shows an oxidation potential of 1.31 V against a standard calomel electrode in acetonitrile solvent. This potential is well below the potential for the oxidation of $O_2$, CO, or $CO_2$ to cationic species. However, the oxidation potential of $NO_2^+$ is relatively close at 1.27 V against a standard calomel electrode in acetonitrile. The nitrosyl cation ($NO_2^+$) is considerably larger than the nitrosonium cation ($NO^+$), however, and it should have much lower ionic conductivity through the solid electrolyte, if it fits at all into the channels 30 of the solid electrolyte structure. Although the oxidation-reduction potential at a platinum-solid electrolyte interface will be different from that found on a standard calomel electrode at room temperature in an organic solvent, the basic ordering of redox potentials should be maintained. Referring now to FIG. 7 of the drawing, the bipotentiostat electrochemical detector using concentric ring-disk type electrodes for nitric oxide is preferably constructed according to the following steps:

1. depositing a reference electrode 66 onto a substrate 70;
2. sputter depositing amorphous metal cation alumina 68 onto the substrate 70 and over the reference electrode 66;
3. placing spaced-apart first and second porous working electrodes 60 and 62 onto the alumina 68;
4. sputter depositing additional amorphous metal cation alumina 68 between the working electrodes 60 and 62;
5. heating the amorphous metal cation alumina to a sufficient temperature to convert the amorphous alumina to β-alumina or β"-alumina;
6. ion exchanging the metal cations of the alumina for nitrosonium cations; and
7. placing a counter electroche 64 to complete a bipotentiostat arrangment of the electrodes;

whereby the first and second working electrodes 60 and 62 are separated by a mobile cation solid electrolyte 68 that is highly selective to the conductivity of nitrosonium cations.

It should be appreciated that the exact sequence of steps is not critical to the method and the sequence and details of the steps can be modified by those skilled in the art.

The presently most preferred substrate 70 is single crystal sapphire. Sapphire is a preferable material because it has similar thermal expansion coefficients as alumina and is less likely to be cracked during heating in manufacturing process steps. However, it is anticipated that mica, quartz, and spinel-($MgAl_2O_4$) and similar materials would also be suitable substrates.

The step of depositing the reference electrode 66 onto the substrate 70 can be performed by vapor depositing or sputter depositing techniques, both of which are well known to those skilled in the art. The shape of the deposited electrode 66 can be controlled, for example, through the use of masking or lithographic techniques.

Figure 8:
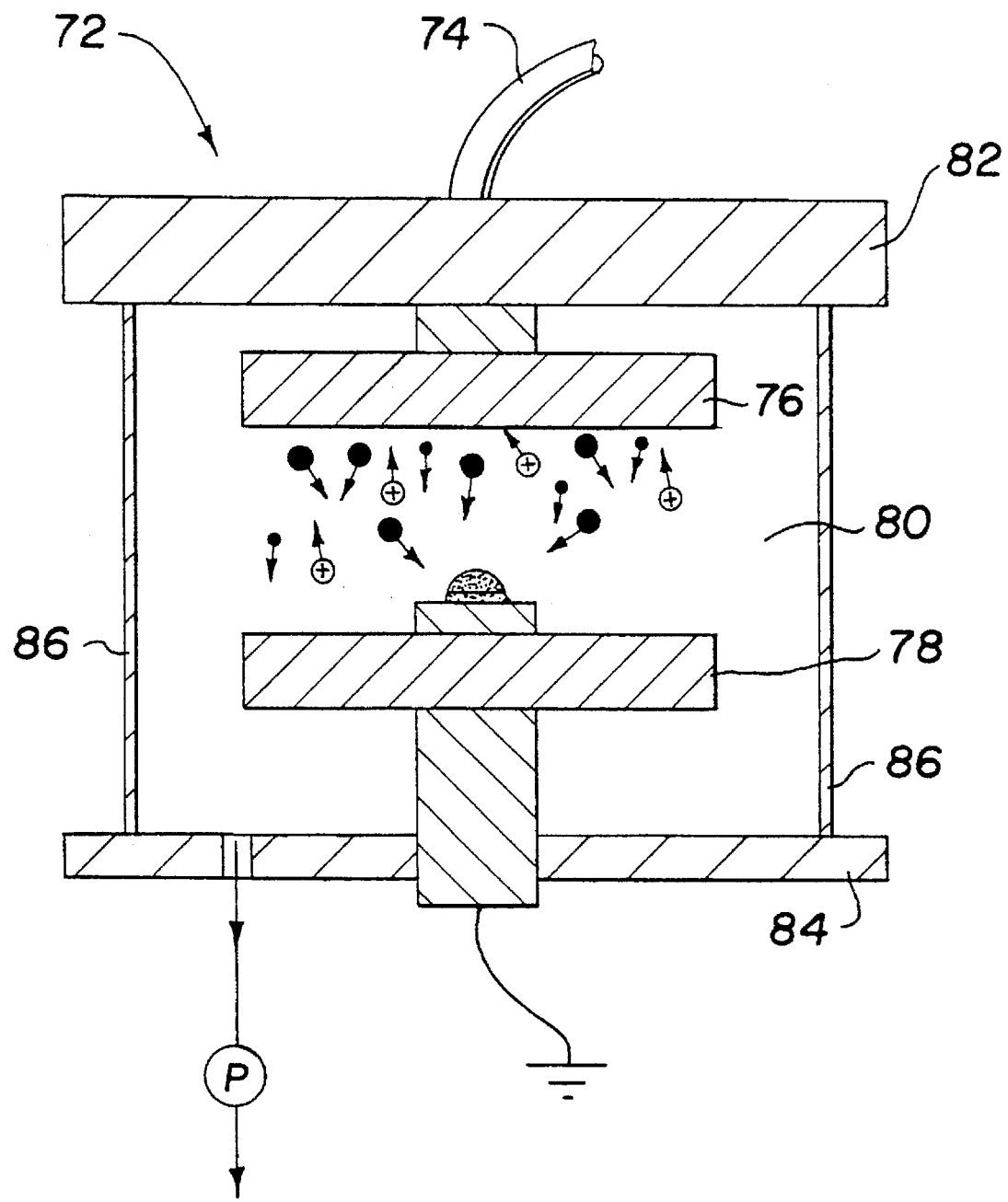
FIG. 8 represents the apparatus for sputter depositing alumina onto a substrate.

Referring briefly to FIG. 8 of the drawing, the operation of a typical sputtering apparatus 72 is shown. RF-sputtering of the alumina has the advantage of being able to be used in a production setting to reproducibly prepare high quality films of material.

The apparatus 72 includes a high voltage line 74 connected to a cathode target 76 and an anode 78 being connected to ground. The cathode target 76 and the annode 78 are enclosed in a chamber 80 defined by walls 82, 84, and 86.

Each substrate can be prepared by ultrasonic cleaning in aqueous Alconox® alkaline detergent for at least 30 minutes, rinsing with deionized water, rinsing with acetone, and drying in an oven maintained at about 135° C. Prepared substrates can be transferred to a Plasmatic Systems microwave plasma etcher and etched for 10 minutes at 600 Watts in air plasma at approximately 10 mTorr.

Sputter depositions can be performed in sputter apparatus such as a VTA triple 6-inch target, 13.56 MHz RF planar magnetron sputtering apparatus 72. Two 2 by 3 inch and three 1 by 3 inch microscope slides can be arranged directly on the J-arm drum or on a 6 inch diameter by 0.25 inch fused quartz plate on the J-arm drum. Sapphire substrate disk 70 can be placed centrally on one of the larger microscope slides. Close by, at approximately the same distance from the plate center, two 4 mm by 8 mm rectangular tungsten carbide wafers can be placed to mask a small portion of the slide.

A vacuum in chamber 80 is created by evacuated to approximately 100 mTorr with a roughing pump, then isolated from the roughing pump and evacuated to $1\times10^{-4}$ Torr with a cryopump 76. Argon and oxygen are metered in the chamber to bring total chamber pressure up to $2\times10^{-3}$ Tort. Chamber atmosphere composition is preferably about 90% argon and 10% oxygen.

With the substrate on the annode side of the chamber 80 and the cathode target covered by a shutter, RF power can be applied to the target and brought slowly up to the desired final power level. Once the final power level is reached, the J-arm can be routed under the target and timing begun. After the desired deposition time, the J-arm can be rotated away from the target and power to the target can be gradually reduced to zero. After cool down, the chamber 80 can be vented with air. Deposition thickness can be determined by tracing the masked regions of one slide with a Taylor-Hobson profilometer.

The deposited thin films are heated in a bed of freshly prepared polycrystalline Na-β-alumina powder to between 600° C. and 1500° C. for up to 90 minutes in air. This results in the irreversible conversion of the amorphous alumina to β-alumina or β"-alumina in which there is a preferred orientation of the conduction channels parallel to the film surface. For example, if heated to 1500° C., conversion of the amorphous β-alumina takes place in about 10–15 minutes. The processed film can be characterized by X-ray diffraction to make sure the conversion is complete.

Figure 9:
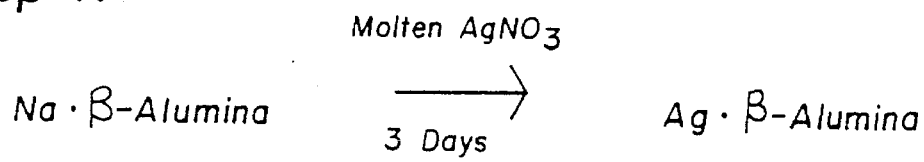
FIGS. 9 and 10 show the chemical reactions for converting Na-β-alumina to NO-β-alumina.
Figure 10:
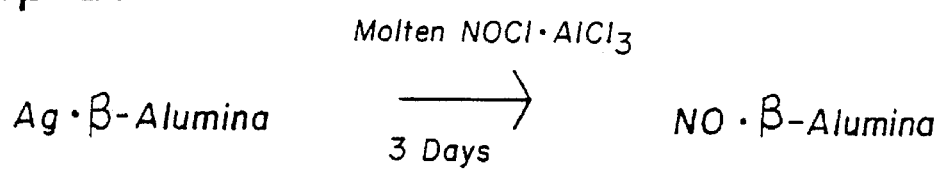

Referring now to FIGS. 9 and 10 of the drawings, the Na-β-alumina is preferably converted to NO-β-alumina in a two step process. In the first step, which is shown in FIG. 9, the Na-β-alumina is ion exchanged with $Ag^+$ to Ag-β-alumina utilizing $AgNO_3$ melt, according to chemistry that is well known in the art. In the second step, which is shown in FIG. 10, the Ag-β-alumina is ion exchanged with $NO^+$ to NO-β-alumina utilizing NOCl.

Figure 11:
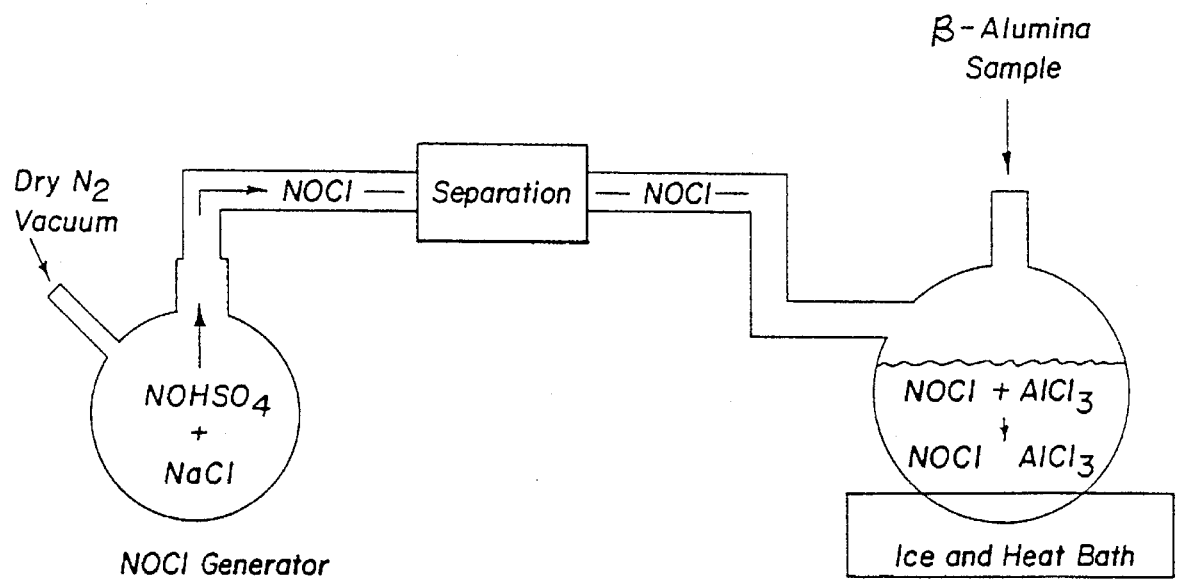
FIG. 11 illustrates the chemical process of $NO^+$ ion exchange for Na-β-alumina.

The second step is further illustrated in FIG. 11. Equimolar mounts of $NOHSO_4$ and NaCl are heated in a round bottom flask and the gas generated is collected using a cold trap. A known mount of this gas of NOCl is re-evaporated to collect in a round bottom flask containing freshly sublimed $AlCl_3$. This flask was heated slowly to 190° C. and Ag-β-alumina thin film was added to this molten NOCl•$AlCl_3$. Care is taken to perform the reaction in a completely dry atmosphere, and the film was dried in vacuum. The ion exchange was found to be complete after 5–6 hours of reaction. The ion exchanged film was characterized using X-ray diffraction, which shows very little disruption of the β-alumina structure during the ion-exchange process, and infrared spectroscopy which shows a characteristic $NO^+$ absorption peak. Quantitative Thermal analysis experiments confirm that the two step process results in about 85% of the cations being exchanged for $NO^+$.

Ion exchange of Ag-β-alumina to NO-β-alumina requires a medium that is a good solvent for both $NO^+$ and $Ag^+$ and has oxidative stability at temperature approaching 20° C. Although $NOAlCl_4$ melts can be used at 198° C. and are presently the most preferred for the ion exchange process, other preferred compositions include mixtures of $NO^+X^-$ salts with organic solvents such as polynitrobenzenes and/or $AlCl_3$-n-alkylammonium pyridinium halides or other quaternary ammonium halides, where $X^-$ is a nucleophilic artion such as $PF_6^-$.

The description and drawings of the specific examples above do not point out what an infringement of this patent would be, but are to provide at least one explanation of how to make and use the invention. Numerous modifications and variations of the preferred embodiments can be made without departing from the scope and spirit of the invention. Thus, the limits of the invention and the bounds of the patent protection are measured by and defined in the following claims.

Having described the invention, what is claimed is:

1. A method of making an electrochemical detector for detecting nitric oxide, the method comprising the steps of:

(a) depositing a reference electrode onto a substrate:

(b) sputter depositing amorphous metal cation alumina onto the substrate and over the reference electrode:

(c) depositing spaced-apart first and second porous working electrodes onto the metal cation alumina;

(d) sputter depositing additional amorphous metal cation alumina to fill the spaces between the porous electrodes;

(e) heating the amorphous metal cation alumina to a sufficient temperature and for a sufficient time to convert the amorphous alumina to an alumina selected from the group consisting of β-alumina, β"-alumina, and any combination thereof;

(f) ion exchanging the metal cations of the alumina for nitronium cations; and (g) contacting a counter electrode to the alumina; whereby the reference electrode, the first and second working electrodes, and the counter electrode form a bipotentiostat arrangement and the first and second working electrodes are separated by a mobile cation solid electrolyte that is highly selective to the conductivity of nitrosonium cations.

2. The method of making an electrochemical detector for nitric oxide according to claim 1, wherein the substrate is selected-from the group consisting of: sapphire, alumina, and spinel-($MgAl_2O_4$).

3. The method of making an electrochemical detector for nitric oxide according to claim 1, wherein the step of depositing a reference electrode onto a substrate further comprises the step of vapor depositing the electrode material onto the substrate.

4. The method of making an electrochemical detector for nitric oxide according to claim 1, wherein the step of depositing a reference electrode onto a substrate comprises the step of sputter depositing the electrode material onto the substrate.

5. The method of making an electrochemical detector for nitric oxide according to claim 1, wherein the metals for the reference electrode, the first and second working electrodes, and counter electrode are independently selected from the group consisting of silver, platinum, palladium, and gold.

6. The method of making an electrochemical detector for nitric oxide according to claim 1, wherein the step of depositing spaced-apart first and second porous working electrodes onto the metal cation alumina further comprises: lithographically depositing the first and second porous working electrodes in a concentric bipotentiostat arrangement.

7. The method of making an electrochemical detector for nitric oxide according to claim 1, wherein the metal cation of the amorphous metal cation alumina is selected from the group consisting of: sodium, potassium, and silver cations.

8. The method of making an electrochemical detector for nitric oxide according to claim 1, wherein the metal cation of the amorphous metal cation alumina is selected from the group consisting of: sodium and potassium cations.

9. The method of making an electrochemical detector for nitric oxide according to claim 8, wherein the step of ion exchanging the metal cations of the alumina for nitronium cations further comprises the steps of: converting the sodium or potassium alumina to silver alumina by ion-exchange with molten silver nitrate; and then converting the silver alma to nitronium alumina by ion-exchange with molten NOCl•$AlCl_3$.

10. The method of making an electrochemical detector for nitric oxide according to claim 1, wherein the step of heating the amorphous metal cation alumina to a sufficient temperature to convert the amorphous alumina to β-alumina or β"-alumina comprises heating the alumina to a temperature between 600° C. and 1500° C.

* * * * *

UNITED STATES PATENT AND TRADEMARK OFFICE
CERTIFICATE OF CORRECTION

PATENT NO.   : 5,580,433
DATED        : December 3, 1996
INVENTOR(S)  : Charles K. Baker, Mohan R. A. Ram and Stephen T. Wellinghoff It is certified that error appears in the above-identified patent and that said Letters Patent is hereby corrected as shown below:

Column 1,
Line 35, begin new paragraph with "In";

Column 2,
Line 46, change the word "Fietrick" to -- Hietrick --;
Line 49, place a comma after the word "type";

Column 3,
Line 41, change the word "Node" to -- Noda --;
Line 41, change the word "Karo" to -- Kart --;
Line 42, change the word "Karachi" to -- Kurachi --;

Column 4,
Line 19, after the "+" place a -- ) --;
Line 27, the word "artionic" should be -- anionic --;
Line 53, change the letter "t" in "Nation" to -- f --;

Column 5,
Line 22, the word "tint" should be -- first --;

Column 7,
Line 32, after "material" insert -- 26 --;

Column 8,
Line 18, change "41)" to -- 40 --;

Column 9,
Line 19, begin new paragraph with "The";
Line 24, after "of" insert -- $NO_2 \rightarrow$ --;
Line 30, begin new paragraph with "Although";
Line 34, begin new paragraph with "Referring";

Column 10,
Line 37, change the word "Tort." to -- Torr. --;
Line 43, change the word "routed" to -- rotated --;

UNITED STATES PATENT AND TRADEMARK OFFICE
CERTIFICATE OF CORRECTION

PATENT NO. : 5,580,433
DATED : December 3, 1996
INVENTOR(S) : Charles K. Baker, Mohan R. A. Ram and Stephen T. Wellinghoff It is certified that error appears in the above-identified patent and that said Letters Patent is hereby corrected as shown below:

Column 11,
Line 2, change the word "mounts" to -- amounts --;
Line 21, change "20°" to -- 200° --;
Line 28, change the word "artion" to -- anion --;
Line 41, after "substrate" delete the ":" and insert a -- ; --;
Line 43, after "electrode" delete the ":" and insert a -- ; --;

Column 12,
Line 10, after "selected" delete the -- - --;
Line 47, change the word "alma" to -- alumina --.

This certificate supersedes Certificate of Correction issued May 13, 1997.

Signed and Sealed this

Thirteenth Day of May, 2003

JAMES E. ROGAN
*Director of the United States Patent and Trademark Office*